(12) United States Patent
Pronk et al.

(10) Patent No.: US 11,730,399 B2
(45) Date of Patent: Aug. 22, 2023

(54) SYSTEMS AND METHODS TO VISUALIZE ROAMING PATIENT MONITORS

(71) Applicant: KONINKLIJKE PHILIPS N.V., Eindhoven (NL)

(72) Inventors: Serverius Petrus Paulus Pronk, Vught (NL); Johannes Henricus Maria Korst, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/383,490

(22) Filed: Jul. 23, 2021

(65) Prior Publication Data

US 2022/0039694 A1 Feb. 10, 2022

Related U.S. Application Data

(60) Provisional application No. 63/060,720, filed on Aug. 4, 2020.

(51) Int. Cl.
*H04B 17/318* (2015.01)
*H04L 43/12* (2022.01)
*H04W 84/12* (2009.01)
*A61B 5/11* (2006.01)
*A61B 5/00* (2006.01)

(52) U.S. Cl.
CPC .......... *A61B 5/1113* (2013.01); *A61B 5/0015* (2013.01); *A61B 5/742* (2013.01)

(58) Field of Classification Search
CPC .................................................. A61B 5/1113
See application file for complete search history.

(56) References Cited

U.S. PATENT DOCUMENTS

| 2002/0178281 | A1* | 11/2002 | Aizenbud-Reshef | H04L 43/50 702/57 |
| 2008/0222294 | A1* | 9/2008 | Liang | H04W 36/24 709/227 |
| 2008/0228039 | A1* | 9/2008 | Huseth | G08B 21/0492 600/300 |
| 2008/0285462 | A1* | 11/2008 | Baker | H04W 16/18 370/241 |
| 2011/0087663 | A1* | 4/2011 | Tonegawa | G06F 16/164 707/736 |
| 2013/0150012 | A1* | 6/2013 | Chhabra | H04W 48/16 455/418 |

(Continued)

FOREIGN PATENT DOCUMENTS

JP 2012190282 A 10/2012

*Primary Examiner* — Joseph H Feild
*Assistant Examiner* — Pameshanand Mahase (57) ABSTRACT

A non-transitory computer readable medium stores instructions executable by at least one electronic processor to perform a method of tracking patient movement through a medical facility. The method includes: receiving wireless roaming data for a wireless patient device associated to a patient from a wireless electronic data communication network comprising a plurality of access points (APs) dispersed through the medical facility; from the received wireless roaming data, determining a connection history for the wireless patient device indicating the AP connected with the wireless patient device as a function of time; and generating a visualization of the connection history for the wireless patient device.

15 Claims, 4 Drawing Sheets

(56) References Cited

U.S. PATENT DOCUMENTS

| | | | |
|---|---|---|---|
| 2016/0119838 A1* | 4/2016 | Kapoor | H04B 17/318 370/332 |
| 2017/0005911 A1 | 1/2017 | Kasargod | |
| 2019/0130724 A1 | 5/2019 | Harrod, IV | |

* cited by examiner

SYSTEMS AND METHODS TO VISUALIZE ROAMING PATIENT MONITORS

This application claims the benefit of U.S. Provisional Application No. 63/060,720, filed on 4 Aug. 2020. This application is hereby incorporated by reference herein.

The following relates generally to the patient monitoring arts, patient tracking arts, wireless hospital network arts, wireless information technology (IT) arts, and related arts.

BACKGROUND

Wireless patient monitors in hospitals allow patients to be monitored while being mobile, e.g., walking around, or while being transported between the various wards. As a monitor moves through the hospital, it successively connects from one to another access point (AP) while disconnecting from a previous AP (i.e. a roaming event or handover event) in a process called roaming.

Tracking roaming activity of wireless patient devices can be informative for the hospital information technology (IT) department for use in identifying overloaded or underused APs or areas where the AP signal is frequently lost. Tracking of the roaming activity could also be useful to hospital security in tracking down a missing patient, or to nursing staff for locating patients to administer medications or other treatment. Tracking of roaming activity could also be used for workflow efficiency assessment, for example by identifying places where patients are delayed in going to a laboratory or such. However, translating roaming data to a useful format can be difficult. The APs are often distributed across a hospital floorplan in no specific pattern, and the communication ranges of the APs may differ, and even for a given AP the communication range may be directionally dependent due to factors such as radio frequency (RF) absorbing walls, multiple RF reflections, and/or so forth.

The following discloses certain improvements to overcome these problems and others.

SUMMARY

In one aspect, a non-transitory computer readable medium stores instructions executable by at least one electronic processor to perform a method of tracking patient movement through a medical facility. The method includes: receiving wireless roaming data for a wireless patient device associated to a patient from a wireless electronic data communication network comprising a plurality of access points (APs) dispersed through the medical facility; from the received wireless roaming data, determining a connection history for the wireless patient device indicating the AP connected with the wireless patient device as a function of time; and generating a visualization of the connection history for the wireless patient device.

In another aspect, an apparatus for tracking patient movement through a medical facility includes at least one electronic processor programmed to: receive wireless roaming data for a wireless patient device associated to a patient from a wireless electronic data communication network comprising a plurality of APs dispersed through the medical facility; from the received wireless roaming data, determine a connection history for the wireless patient device indicating the AP connected with the wireless patient device as a function of time; and generate a visualization of the connection history for the wireless patient device as a plot of the connection history on an AP-versus-time chart in which the APs are arranged as discrete points on a vertical axis of the AP-versus-time chart and a time duration as a horizontal axis of the AP-versus-time chart.

In another aspect, a method of tracking patient movement through a medical facility includes: receiving wireless roaming data for a wireless patient device associated to a patient from a wireless electronic data communication network comprising a plurality of APs dispersed through the medical facility; from the received wireless roaming data, determining a connection history for the wireless patient device indicating the AP connected with the wireless patient device as a function of time; and generating a visualization of the connection history for the wireless patient device as an AP-versus-time chart with the APs as a vertical axis of the AP-versus-time chart and the time duration as a horizontal axis of the AP-versus-time chart, the APs being arranged on the vertical axis with APs having frequent roam events between them as being close to each other on the vertical axis, and APs having few or no roam events between them as distant from each other.

One advantage resides in tracking patient movement through a medical facility.

Another advantage resides in tracking patient movement through a medical facility based on connection to APs dispersed throughout the medical facility.

Another advantage resides in ordering APs connected to a patient device as the patient moves through a medical facility.

Another advantage resides in providing a visualization of ordered APs connected to a patient device as the patient moves through a medical facility.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Patients moving through the hospital with wireless devices attached or moving with the patients create paths, each consisting of APs to which monitors are successively connected. Visualizing the path that a monitor creates can be done in several ways. One way is to construct a graph, based on this path, to draw the graph in two dimensions, and to draw the path along the edges. A disadvantage of this way of visualizing a path is that the component time is absent. As a result, multiple roaming events between the same pair of APs are not easily distinguished, and identifying the path itself is cumbersome. The following discloses an approach for tracking a patient by way of detecting roaming events, that is, events in which the patient's wireless (e.g. Wi-Fi) monitor switches from a connection to one access point (AP) to another as the patient moves or is moved about. Visualization of these roaming events can be informative for the hospital information technology (IT) department for use in identifying overloaded or underused APs or areas where the AP signal is frequently lost. The visualization could also be useful to hospital security in tracking down a missing patient. The visualization could also be useful for nursing staff for tracking patients. Yet other applications could relate to workflow efficiency assessment, for example by identifying places where patients are delayed in going to a laboratory or such. In addition, a wireless device may successively be connected to different patients. Additional data, such as bed assignments or patient assignments, may separate one patient track from another on the visualization.

A straightforward approach for visualizing patient movement via roaming data would be to provide a two-dimensional (2D) map of the hospital floor with the APs marked, and superimposing the patient path based on the detected roaming events. However, this would not provide time information, and moreover the area covered by a given AP is fairly large, possibly directionally dependent, and difficult to determine, which can make delineation of a curvilinear path in the 2D map imprecise. Still further, it requires generation of the 2D map and defining the AP locations within it, and updating this information whenever an AP is moved, removed, or added. Moreover, for some applications of roaming data, mapping patient movement in space may be of secondary interest. For example, knowing whether/when the patient is moving can be useful for assessing patient activity, even if the patient's path in space is not mapped. While a precise location of a missing patient would be useful, a determination that the patient is stationary (as indicated by no recent roaming events) may still be of value. Historical roaming data can also be analyzed to identify frequently overloaded or underutilized APs, without need to derive the AP locations from the roaming data. Rather, as recognized herein for such applications visualizing the time dimension of the roaming data may be more important than spatial mapping.

The disclosed approach is to employ a chart of connected AP versus time for a given wireless patient device. The resulting plot is a horizontal line as long as the patient remains connected to an AP, with a vertical jump to a next AP at each roam event when the wireless medical device is handed over to the next AP. This neatly captures the time aspect, and avoids the complexity of attempting to delineate a curvilinear path in two- or three-dimensional space.

However, if the APs are placed along the vertical axis in an arbitrary order, then the vertical jumps at roam events can be essentially random in size and direction (i.e., up versus down). This would result in a cluttered chart that is difficult to visually interpret. Additionally, arbitrary AP placement along the vertical axis would not segregate potentially separate AP networks. One way to address this is to have a designer manually arrange the APs along the vertical axis based on information such as a map of AP placements over the hospital floorplan. However, the manual designer is unlikely to accurately account for factors such as overloading of an AP, or different APs having different and/or directionally dependent wireless signal strengths.

To address this, the illustrative approach processes historical roam data to automatically arrange the APs in the vertical direction so that neighboring APs along the vertical direction have frequent roam events between them, while APs that are distant from each other along the vertical axis have few or no roam events between them. The result is a less cluttered chart in which, for example, it is likely that the patient moving in a single direction will trace small vertical jumps in the chart. Automatically computing the arrangement of the APs in the vertical direction based on roam event frequencies between AP pairs inherently takes into account factors such as AP overloading and different/directionally dependent AP signal strengths, thus ensuring good placement of the APs in the vertical direction without tedious manual AP placements.

Optimally arranging the APs on the vertical axis in this way amounts to solving a Linear Ordering Problem (LOP) for the historical roaming data. The historical roaming data is represented as a weighted, undirected graph in which the nodes are the APs, the edges are roam events (e.g., a roam event from $AP_i$ to $AP_j$ or vice versa corresponds to an edge between $AP_i$ and $AP_j$) and the weights of the edges are counts (optionally normalized) of roam events between the two APs joined by the edge. The disclosed systems and methods also provide various ways of handling a lost connection, mostly based on adding one or more conceptual "EMPTY AP" nodes in the undirected graph. That is, a special AP, called EMPTY, is used which models the situation that a monitor is not connected to any AP, in which case it is said to be connected to the EMPTY AP. The EMPTY AP ensures that a monitor creates only one path. Advantageously, the disclosed LOP solution naturally identifies unconnected (sub-)nets of AP nodes. Furthermore, the approach can be applied to historical roaming data without any a priori knowledge of the hospital floor plan or the spatial layout of the APs on the hospital floor.

The chart itself will in general have a single jumpy line for each tracked wireless patient device. Multiple patients (or, more precisely, multiple patient devices associated to corresponding patients) can optionally be shown on the same chart. Color coding and/or designated EMPTY AP points along the vertical axis can be used to highlight time intervals in which the patient monitor loses connection to the wireless (e.g., Wi-Fi) network entirely. In another variant, color coding could be used to highlight specific patient monitor events such as loss of data transmission capacity, although again such enhancements would be balanced against providing an overly cluttered graphic. In yet another variant, different patients may be plotted in different colors to make it easy to distinguish the different patients.

The visualization can be provided in real time (effectively, as a trend line as it is a chart versus time on the horizontal axis). Such a plot might, for example, be displayed at a nurses' station to track patient activity. Additionally or alternatively, the patient roaming data could be stored and a visualization generated retrospectively for any chosen time interval. Such retrospective visualization may, for example, be useful for IT network and/or workflow analyses.

Figure 1:
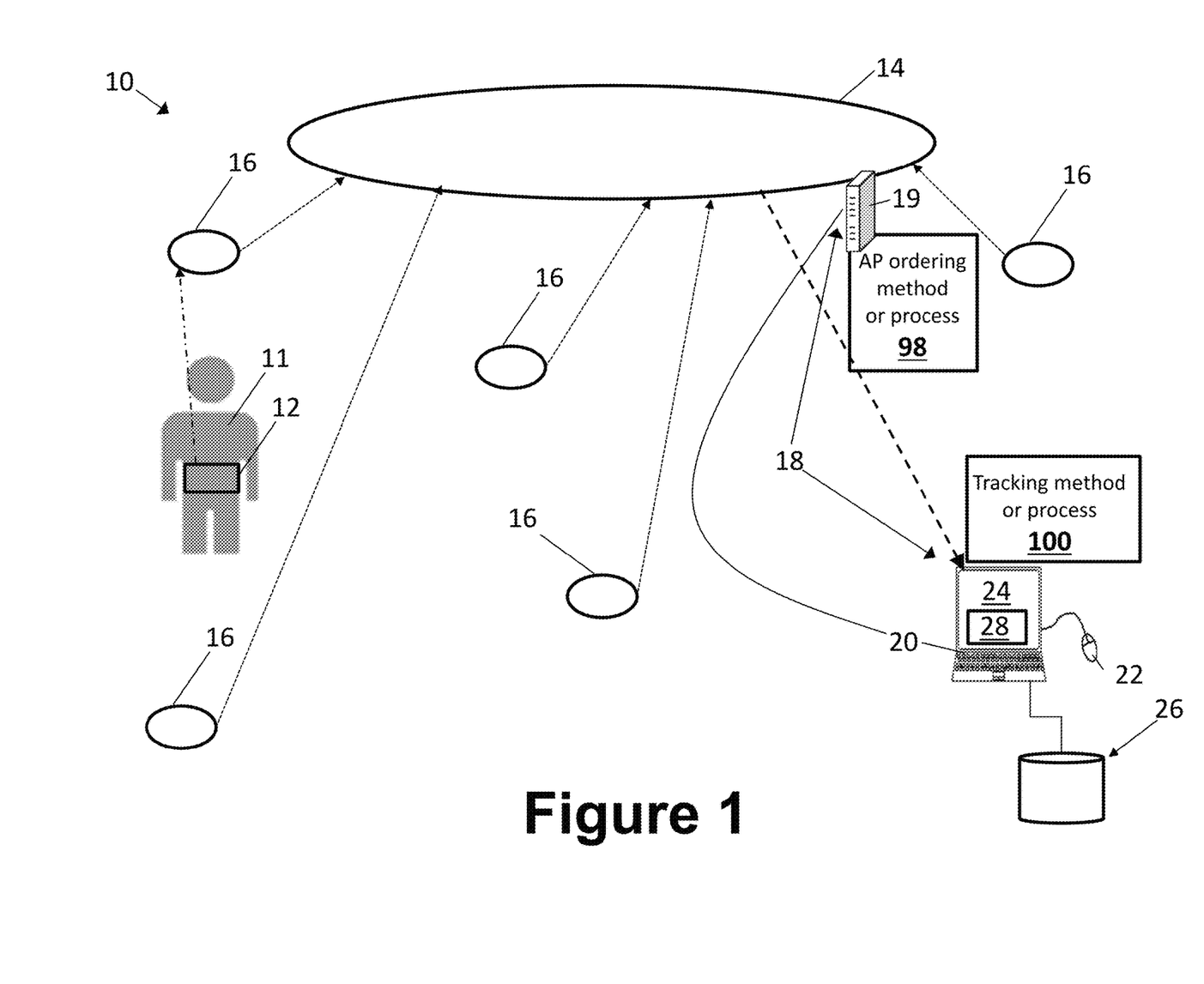
FIG. 1 diagrammatically shows an illustrative apparatus for tracking patient movement through a medical facility in accordance with the present disclosure.

With reference to FIG. 1, an illustrative apparatus 10 is shown for tracking patient movement through a medical facility. The illustrative example provides patient tracking for a hospitalized patient 11 monitored by a wireless patient device 12 (e.g., a patient monitor, wireless-capable infusion pump, wireless patient ID tag, a dedicated wireless patient tracking sensor, and so forth) connected to a wireless electronic data communication network 14 (e.g., a Wi-Fi network) of the medical facility via a plurality of APs 16 dispersed throughout the medical facility. The wireless patient device 12 is associated to the patient 11 insofar as the wireless patient device 12 moves with the patient 11 as the patient moves or is transported through the hospital. Depending upon the nature of the wireless patient device 12, it may be worn by the patient (e.g. a wireless patient ID wristband) or disposed on a wheelchair or gurney (not shown) on which the patient 11 is disposed or connected with the patient via tubing or electrical cable (e.g., a wireless infusion pump connected via an intravenous (IV) tube with a patient IV port), or so forth. FIG. 1 also shows an electronic processing device 18, such as a workstation computer, nurses' station computer or electronic whiteboard, various combinations thereof, or more generally a computer. The electronic processing device 18 may also include a server computer 19 or a plurality of server computers, e.g. interconnected to form a server cluster, cloud computing resource, or so forth, to perform more complex computational tasks. The workstation 18 includes typical components, such as an electronic processor 20 (e.g., a microprocessor), at least one user input device (e.g., a mouse, a keyboard, a trackball, and/or the like) 22, and a display device 24 (e.g. an LCD display, plasma display, cathode ray tube display, and/or so forth). In some embodiments, the display device 24 can be a separate component from the workstation 18, or may include two or more display devices.

The electronic processor 20 is operatively connected with one or more non-transitory storage media 26. The non-transitory storage media 26 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth; and may be for example a network storage, an internal hard drive of the workstation 18, various combinations thereof, or so forth. It is to be understood that any reference to a non-transitory medium or media 26 herein is to be broadly construed as encompassing a single medium or multiple media of the same or different types. Likewise, the electronic processor 20 may be embodied as a single electronic processor or as two or more electronic processors. The non-transitory storage media 26 stores instructions executable by the at least one electronic processor 20. The instructions include instructions to generate a visualization of a graphical user interface (GUI) 28 for display on the display device 24.

The apparatus 10 is configured as described above to perform an AP ordering method or process 98 to optimally arrange the APs in the vertical direction of an AP-versus-time chart for visualizing connection histories for the wireless patient devices, and a patient movement tracking method or process 100. The non-transitory storage medium 26 stores instructions which are readable and executable by the at least one electronic processor 20 to perform disclosed operations including performing the AP ordering method or process 98 and the tracking method or process 100. In some examples, the patient movement tracking method 100 can be computationally complex, and may be advantageously performed at least in part by cloud processing. The AP ordering method or process 98 is independent of the particular patient being tracked, and hence can be performed once to generate the optimal AP ordering along the vertical axis, which is then used for all patient instances of the tracking method or process 100. In the illustrative embodiments the AP ordering method or process 98 solves a computationally complex linear ordering problem (LOP), and is beneficially (although not necessarily) performed on the server computer 19.

Figure 2:
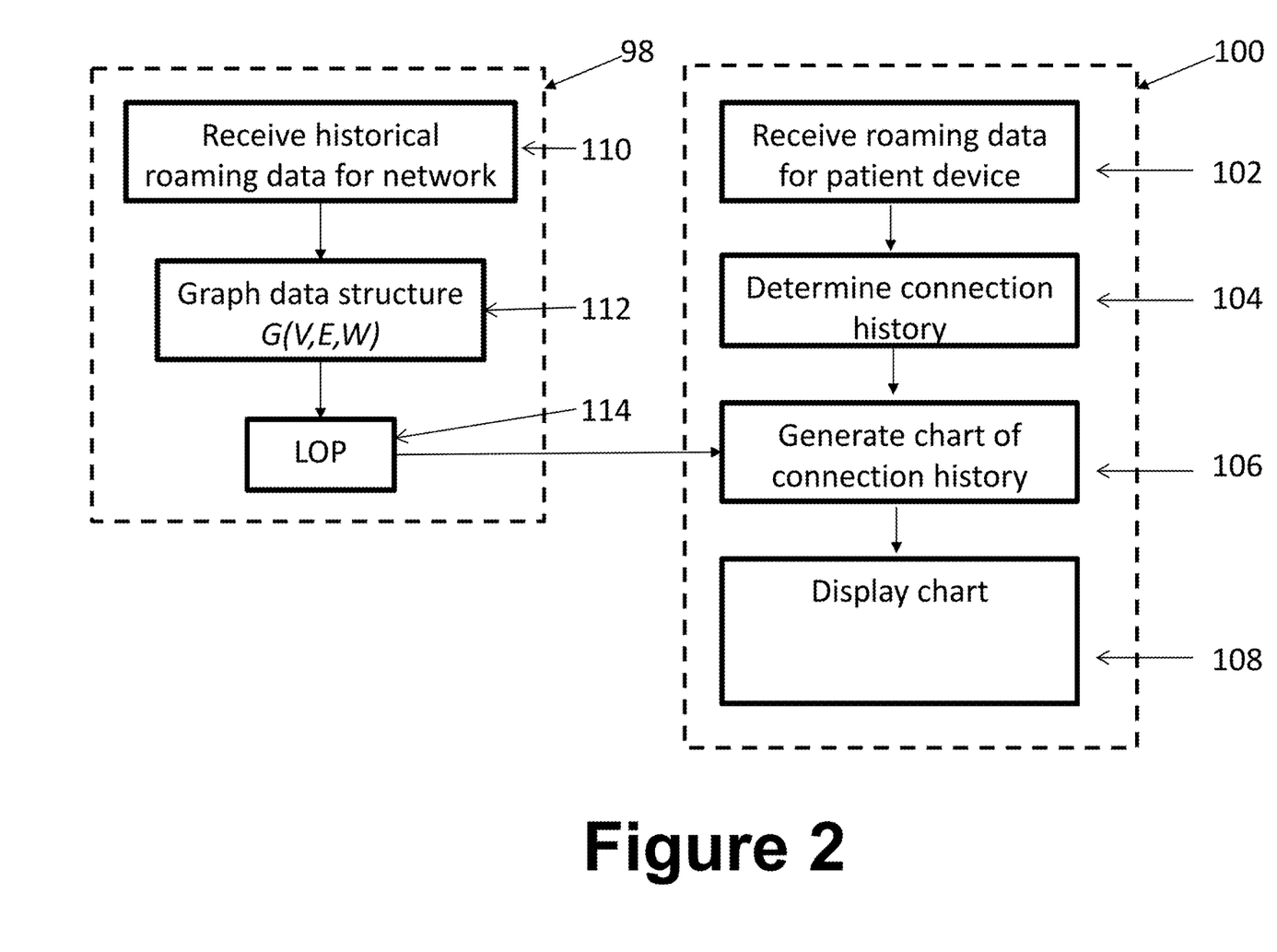
FIG. 2 shows an example flow chart of operations suitably performed by the apparatus of FIG. 1.

With continuing reference to FIG. 1, and with reference to FIG. 2, an illustrative embodiment of the patient movement tracking method 100 is diagrammatically shown as a flow-chart. At an operation 102, the workstation 18 is programmed to receive wireless (e.g., Wi-Fi) roaming data for the wireless patient device from the APs 16 of the network 14. In some example, the Wi-Fi roaming data is received in real time, while in other examples, the Wi-Fi roaming data is received and stored in the non-transitory computer readable medium 26. At an operation 104, a connection history is determined for the wireless patient device 12. The connection history indicates which AP 16 is connected to the wireless patient device 12 as a function of time. At an operation 106, a visualization of the connection history is generated. At an operation 108, the visualization is displayed on the display device 24 of the workstation 18. In some examples, the visualization can be displayed in real-time as a trendline as the Wi-Fi roaming data is being received at the operation 102.

Figure 3:
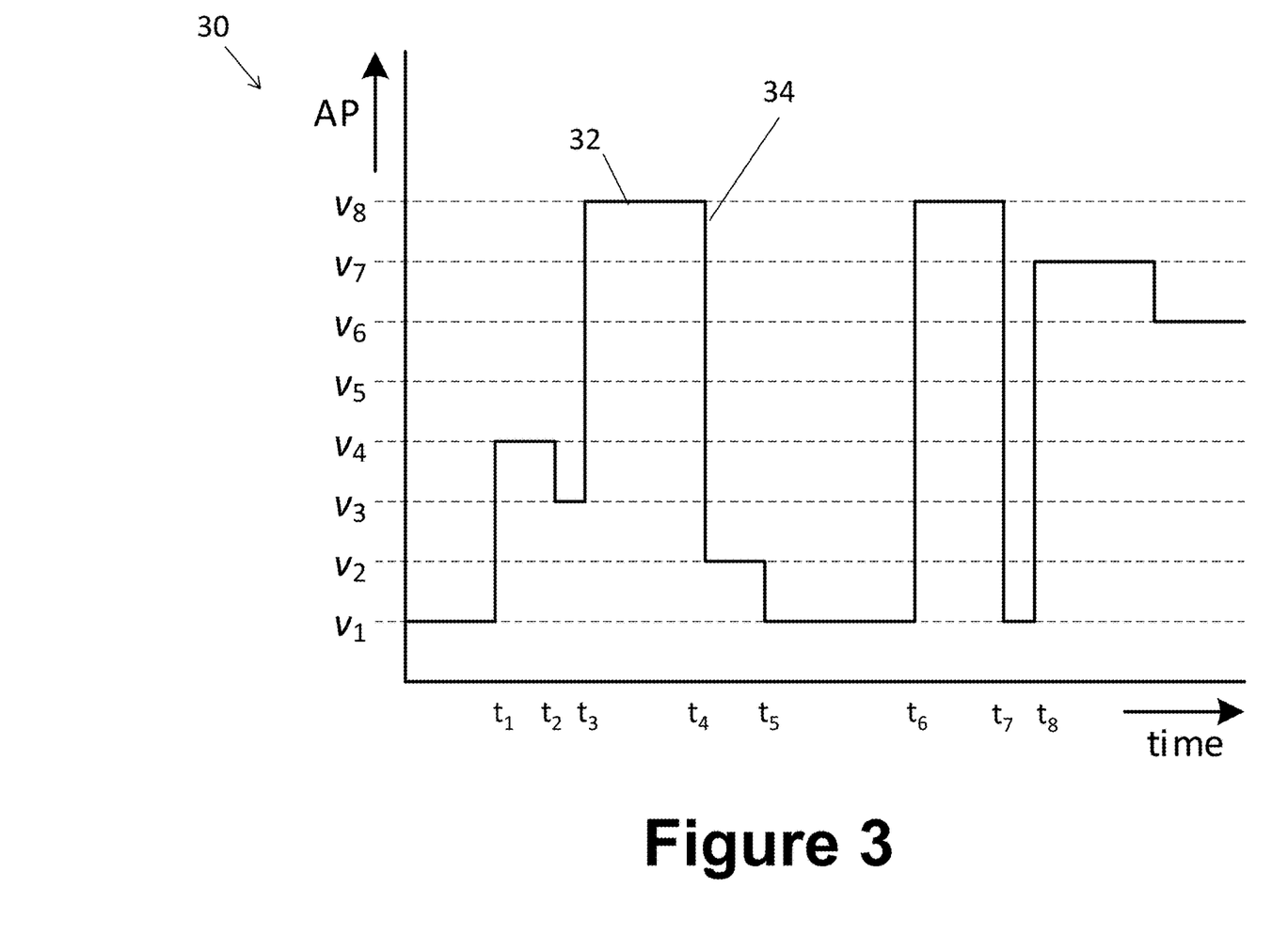
FIG. 3 shows an example of an output generated by the apparatus of FIG. 1.

With continuing reference to FIGS. 1 and 2, and now referring to FIG. 3, an example of the visualization 30 is shown. As shown in FIG. 3, the visualization 30 comprises an AP-versus-time chart, in which the APs 16 are arranged on a vertical axis (i.e., y-axis) of the chart, and the time duration of when the wireless patient device 12 is connected to an AP is arranged as a horizontal axis (i.e., x-axis) of the chart.

The connection history for the wireless patient device 12 can be plotted on the chart 30 as disjoint horizontal lines in which each horizontal line vertically aligns with the single discrete value on the vertical axis of a corresponding AP 16. For each continuous time interval $(t_i, t_j)$ of the connection history over which the wireless patient device 12 is connected with a single AP 16, a horizontal line segment 32 is plotted as running from time $t_i$ to time $t_j$ that is vertically aligned with the single discrete value on the vertical axis that represents the single AP to which the wireless patient device is connected over the continuous time interval $(t_i, t_j)$. For example, as shown in the chart 30 of FIG. 3, the wireless patient device 12 is connected to a first AP 16 labeled as $v_1$ on the y-axis until a time duration $t_1$. At the time $t_1$, the wireless patient device 12 is handed off from the AP 16 labeled vi to a second AP labeled $v_4$, and so forth. For each handover event, a vertical line segment 34 is plotted extending between the two single discrete values on the vertical axis that represent the two APs 16 involved in the handover event.

The APs 16 are arranged on the vertical axis by the AP ordering method or process 98 as APs having frequent roam events between them as being close to each other on the vertical axis, and APs having few or no roam events between them as distant from each other. For example, as shown in FIG. 3, the APs 16 labeled as $v_1$ and $v_2$ are adjacent to each other on the y-axis, and thus have frequent roam events between them; whereas the APs labeled $v_1$ and $v_8$ are distant from each other the y-axis, and thus have few or no roman events between them.

Each AP 16 is represented on the vertical axis as a single discrete value. In some examples, at least one discrete value on the vertical axis can represent "an empty AP", in which the wireless patient device 12 is not connected with any of the APs. In some embodiments, the receiving and the determining operations 102, 104 is performed for a plurality of wireless patient devices 12 associated to corresponding patients, and the visualization 30 includes plotting the connection histories for the plurality of wireless patient devices on a single AP-versus-time plot. To represent differences between the multiple patients, the visualization 30 includes color coding the horizontal line 32 segments to distinguish between the multiple patients.

With returning reference to FIG. 2, and illustrative embodiment of the AP ordering method or process 98 is shown. At an operation 102, the workstation 18 is programmed to receive historical Wi-Fi roaming data for the APs 16 of the network 14. This historical roaming data is for many wireless medical devices of many patients, and may also include roaming data for wireless medical devices that are not associated to a patient, such as cellphones carried by hospital personnel. The historical roaming data is representative of typical network traffic. At an operation 112, a graph data structure is generated, as will be described further below. At an operation 114, a linear ordering problem (LOP) is performed for the weighted undirected graph generated at operation 112 in order to minimize a distance travelled between APs (see, e.g., Diaz, Petit & Serna, A survey of Graph Layout Problems, Universtat Politècnica de Catalunya (2002)). The output of the LOP 114 is a one-dimensional ordered list of the APs 16, which then serves as the placement of the APs along the vertical axis in the AP-versus-time chart generated at operation 106 of the patient movement tracking method or process 100. It should be noted that this arrangement of APs along the vertical axis of the AP-versus-time chart need only be computed once, and can then be re-used for each instance of the operation 112. For example, different instances of the patient movement tracking method or process 100 may be used to track patient movement for different patients or groups of patients; but in each instance of the patient movement tracking method or process 100 the same arrangement of APs along the vertical axis of the AP-versus-time chart produced by the AP ordering method or process 98 can be used. In some examples, the list of APs 16 can be filtered to contain only those APs involved in the roaming path of the one or more wireless patient devices 12.

The graph data structure 112 can be represented as for a weighted, undirected graph G (V, E, W) where V is a set of nodes representing the set of APs of the wireless electronic data communication network, E is a set of undirected edges where $e_{ij} \in E$ is an edge connecting node $v_i \in V$ and $v_j \in V$, and W is a function that assigns edge weights to the edges of the set E. The edge weights have nonnegative values and the edge weight $w_{ij} \in W$ for the edge $e_{ij} \in E$ has a value corresponding to a handover frequency between the pair of APs represented by nodes $v_i, v_j \in V$ in historical roaming data for the wireless electronic data communication network 14. It should be noted that the graph data structure 112 is a mathematical construct (i.e. data structure) that is processed by the LOP 114, and hence the graph data structure 112 does not necessarily need to be displayed on a computer screen or otherwise visualized.

EXAMPLE

The following describes an approach of solving the LOP problem to arrange the APs 16 on the vertical axis of the visualization 30. The historical roaming data received at operation 110 are used, and this data may include all roaming events occurring over a time span of, for example, a few months. The roaming events are used in the operation 112 to create the weighted, undirected graph G(V,E,W) where V are nodes of the graph, E are edges of the graph connecting pairs of nodes (i.e. pairs of APs), and W are weights assigned to the nodes. Its nodes V represent the APs 16 and the edges E are defined by roam events, e.g. an edge between $AP_i$ and APs represents handover events from $AP_i$ to $AP_j$ or vice versa, the weights W assigned to the respective edges are determined by the sum over all wireless patient devices of the number of times that m has roamed between the associated nodes. To be more precise there is an edge between two nodes n and n' if and only if there are at least k roaming (i.e. handover) events that directly go from the AP indicated by node n to the AP indicated by node n' or from the AP indicated by node n' to the AP indicated by node n, where k can be chosen equal to 1, or possibly larger than 1.

This weighted graph is processed by the LOP optimization operation 114. In one approach, a heuristic algorithm can be used in the operation 114 to find a good ordering among the APs 16. This ordering is used for the arrangement of APs along the vertical axis of the AP-versus-time chart generated at the operation 106 of each instance of the tracking method or process 100 to visualize paths from one or more wireless patient devices 12.

The creation of the graph G(V,E,W) is realized by maintaining a mapping from AP pairs to roaming event counts. The weights W of the respective edges E are computed by increasing the appropriate counts. Optionally, the weights may be normalized, e.g. to represent a rate of handover events per day for each AP pair. This creates the graph G(V,E,W) against which the LOP optimization 114 is performed. There are various heuristic algorithms available for solving an LOP problem. In the following, an illustrative heuristic algorithm for solving the LOP problem in the context of optimizing ordering of the APs 16 is described.

Once the graph operation 112 is complete, to start the LOP optimization 114 the AP pairs are ordered in a list designated here as C in order of non-increasing counts. A set S of lists of APs 16 is maintained, where each list represents a consecutive portion of the one list to be realized eventually. Hence, an AP 16 does not occur in multiple lists. Initially, the set S is empty.

Figure 4A:
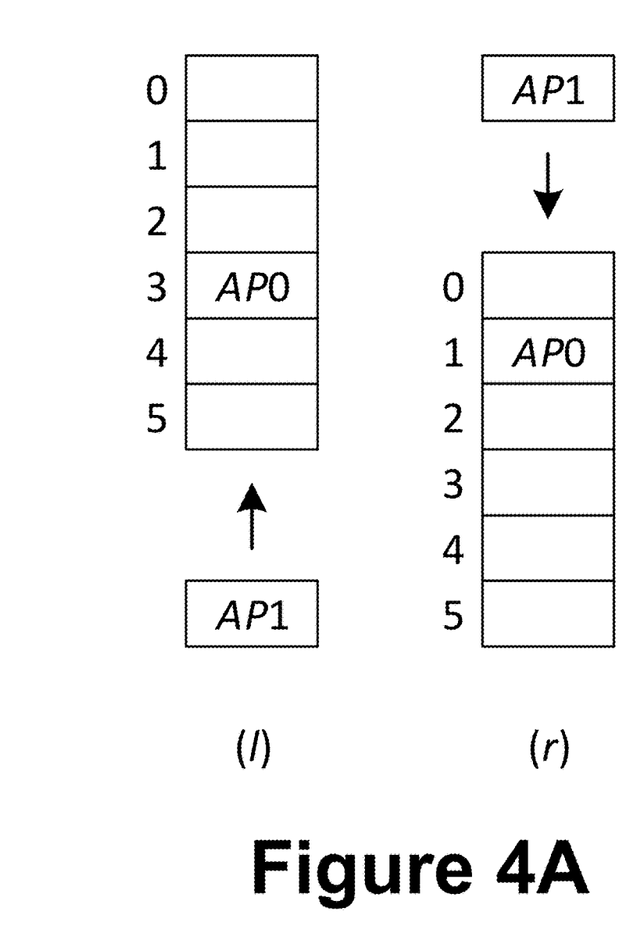
FIGS. 4A and 4B show examples of processes performed by the apparatus of FIG. 1.
Figure 4B:
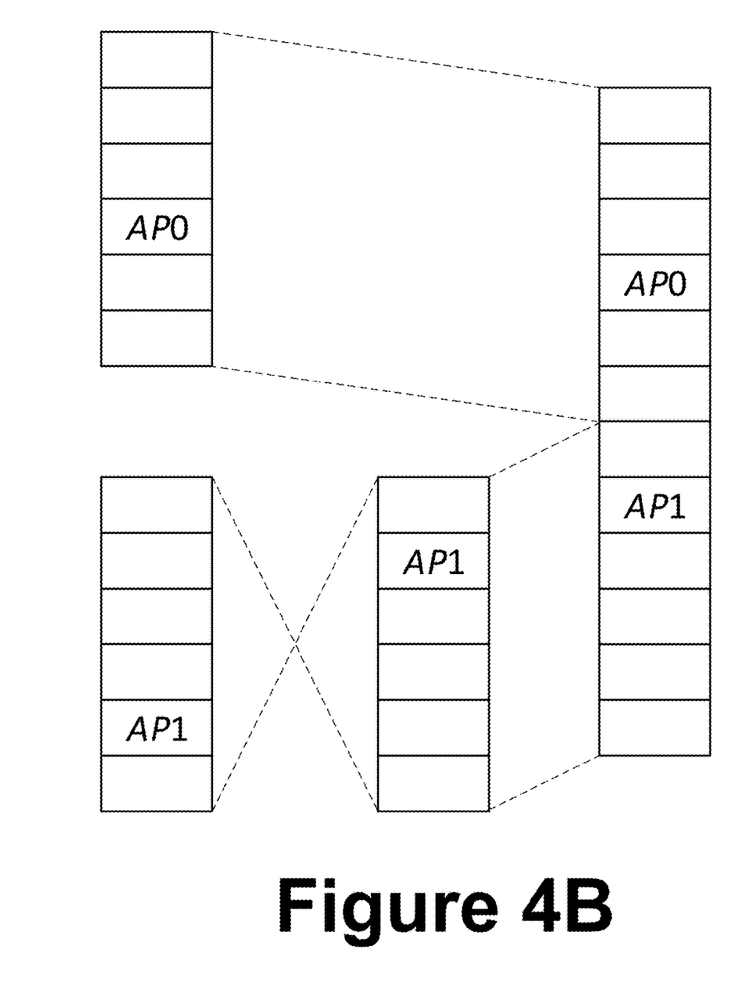

With reference to FIGS. 4A and 4B, as the algorithm chooses the successive AP pairs from list C, four possibilities are possible (here the pair of APs 16 are denoted by $AP_0$ and $AP_1$): (1) if both APs already appear in the same list in the set S, then nothing needs to be done; (2) if neither of these APs occur in any of the lists in the set S, a new list is created, consisting of the two APs, e.g., ($AP_0$ and $AP_1$); (3) if, on the other hand, and without loss of generality, only $AP_0$ already occurs in a list s, and $AP_1$ does not yet appear in any list in S, then $AP_1$ is appended at one end of the list s, where this end is defined as the end that is closest to $AP_0$, where ties are broken arbitrarily. Hence, if l is the length of s, and the position of $AP_1$ in l is $p \in \{0, 1, \ldots, 1-1\}$, then $AP_1$ is appended at the beginning of s if $p \leq \frac{1}{2}$ and at the end otherwise (both situations are illustrated in FIG. 4A, (l) and (r), respectively); and (4) if both APs already appear in two different lists, then the lists are combined into one by appending one to the other, where, if necessary, one of the list may be reversed to ensure that $AP_0$ and $AP_1$ are as close as possible to each other in the combined lists (FIG. 4B shows an example of this process).

When the list C has been exhausted, all final lists in the set S are appended to each other to form one final list. All final lists in the set S correspond to different, unconnected networks, as there are no two APs in different lists that appeared as a pair in the list C.

An EMPTY AP can be treated as an ordinary AP 16. Alternatively, this EMPTY AP may be skipped by not considering any AP pairs where one of the APs is the EMPTY AP. After the process above has completed, the EMPTY AP can be inserted into the final list at an appropriate position, e.g., where the increase in total vertical distance due to this insertion is minimal. A simple iteration over all possible positions does the job, whereby the information in list C, including those elements involving the EMPTY AP are also considered in the calculations.

Another alternative is to insert the EMPTY AP into each of the final lists in the set S before they are appended to each other. These insertion steps are essentially the same as the insertion step in the final list as described above. When the list is filtered for a specific path, the appropriate "copy" or "copies" of the EMPTY AP should be selected.

Another alternative is not to add the EMPTY AP to the list or lists, but instead draw a non-vertical line segment from the AP just before the disconnect to the AP just after the disconnect. By using different colors, a distinction can be made between direct connections between APs and a connection between APs between which a disconnect has occurred, by which a distinction can be made between vertical and nearly vertical line segments.

As previously noted, the foregoing LOP optimization is merely an illustrative example, and it will be appreciated that other LOP optimization algorithms may be employed.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A non-transitory computer readable medium storing instructions executable by at least one electronic processor to perform a method of tracking patient movement through a medical facility, the method comprising:
receiving wireless roaming data for a wireless patient device associated to a patient from a wireless electronic data communication network comprising a plurality of access points (APs) dispersed through the medical facility;
from the received wireless roaming data, determining a connection history for the wireless patient device indicating the AP connected with the wireless patient device as a function of time duration, the connection history indicating at which the wireless patient device is connected to one of the APs of the plurality of APs;
generating a visualization of the connection history for the wireless patient device; wherein the generating included generating an AP-versus-time chart wherein:
time duration is arranged on a first axis; and
the APs are arranged on a second axis by evaluating a linear ordering problem (LOP) for a weighted undirected graph G(V, E, W) where V is a set of nodes representing the set of APs of the wireless electronic data communication network, E is a set of undirected edges where $e_{ij} \in E$ is an edge connecting node $v_i \in V$ and $v_j \in V$, and W is a function that assigns edge weights to the edges of the set E wherein the edge weights have nonnegative values and the edge weight $w_{ij} \in W$ for the edge $e_{ij} \in E$ has a value corresponding to a handover frequency between the pair of APs represented by nodes $v_i, v_j \in V$ in historical roaming data for the wireless electronic data communication network; and
wherein APs having frequent roam events between them are charted being close to each other and APs having few or no roam events between them are charted distant from each other.

2. The non-transitory computer readable medium of claim 1, wherein the arranging of the APs on the second axis of the AP-versus-time chart represents each AP as a single discrete value.

3. The non-transitory computer readable medium of claim 2, wherein the arranging of the APs on the second axis of the AP-versus- time chart further includes arranging at least one discrete value representing an empty AP in which the wireless patient device is not connected with an AP.

4. The non-transitory computer readable medium of claim 3, wherein the generating of the visualization further includes:
for each continuous time interval $(t_i, t_j)$ of the connection history over which the wireless patient device is connected with a single AP, plotting a horizontal line segment running from time $t_i$ to time $t_j$ that is aligned with the single discrete value that represents the single AP to which the wireless patient device is connected over the continuous time interval $(t_i, t_j)$.

5. The non-transitory computer readable medium of claim 4, wherein the visualization includes color coding the line segments to distinguish between multiple wireless patient devices connected to one or more of the APs.

6. The non-transitory computer readable medium of claim 2, wherein the generating of the visualization further includes:
plotting the connection history on the AP-versus-time chart as disjoint lines that align with the single discrete value.

7. The non-transitory computer readable medium of claim 6, wherein the plotting further includes:
for each handover event, plotting a line segment extending between the two single discrete values that represent the two APs involved in the handover event.

8. The non-transitory computer readable medium of claim 1, wherein the receiving and the determining is performed for a plurality of wireless patient devices associated to corresponding patients, and the visualization includes plotting the connection histories for the plurality of wireless patient devices on a single AP-versus-time plot.

9. The non-transitory computer readable medium of claim 1, wherein the method further comprises:
displaying the visualization on a display device in real time as a trendline as the wireless roaming data is being received.

10. The non-transitory computer readable medium of claim 1, wherein:
the receiving of the wireless roaming data includes retrieving the wireless roaming data from the non-transitory data storage, wherein the determining and generating are performed after the retrieving; and the method further comprises:
displaying the visualization on a display device.

11. An apparatus for tracking patient movement through a medical facility, the apparatus comprising at least one electronic processor programmed to:
receive wireless roaming data for a wireless patient device associated to a patient from a wireless electronic data communication network comprising a plurality of access points (APs) dispersed through the medical facility;
from the received wireless roaming data, determine a connection history for the wireless patient device indicating the AP connected with the wireless patient device as a function of time duration, the connection history indicating at which the wireless patient device is connected to one of the APs of the plurality of APs; and generate a visualization of the connection history for the wireless patient device as a plot of the connection history on an AP-versus-time chart in which the APs are arranged as discrete points on a vertical axis of the AP-versus-time chart and the time duration as a horizontal axis of the AP-versus-time chart;

wherein the generating of the visualization includes:

arranging the APs on the vertical axis with APs by evaluating a linear ordering problem (LOP) for a weighted undirected graph $G(V, E, W)$ where V is a set of nodes representing the set of APs of the wireless electronic data communication network, E is a set of undirected edges where $e_{ij} \in E$ is an edge connecting node $v_i \in V$ and $v_j \in V$, and W is a function that assigns edge weights to the edges of the set E wherein the edge weights have nonnegative values and the edge weight $w_{ij} \in W$ for the edge $e_{ij} \in E$ has a value corresponding to a handover frequency between the pair of APs represented by nodes $v_i, v_j \in V$ in historical roaming data for the wireless electronic data communication network.

12. The apparatus of claim 11, wherein the generating of the visualization includes:

arranging the APs on the vertical axis with APs having frequent roam events between them as being close to each other on the vertical axis, and APs having few or no roam events between them as distant from each other.

13. The apparatus of claim 11, wherein the generating of the visualization includes:

for each continuous time interval $(t_i, t_j)$ of the connection history over which the wireless patient device is connected with a single AP, plotting a horizontal line segment running from time $t_i$ to time $t_j$ that is vertically aligned with the single discrete value on the vertical axis that represents the single AP to which the wireless patient device is connected over the continuous time interval $(t_i, t_j)$.

14. The apparatus of claim 11, wherein the generating of the visualization includes:

for each handover event, plotting a vertical line segment extending between the two single discrete values on the vertical axis that represent the two APs involved in the handover event.

15. A method of tracking patient movement through a medical facility, the method comprising:

receiving wireless roaming data for a wireless patient device associated to a patient from a wireless electronic data communication network comprising a plurality of access points (APs) dispersed through the medical facility;

from the received wireless roaming data, determining a connection history for the wireless patient device indicating the AP connected with the wireless patient device as a function of time; and generating a visualization of the connection history for the wireless patient device as an AP-versus-time chart with the APs as a vertical axis of the AP-versus-time chart and the time duration as a horizontal axis of the AP-versus-time chart, the APs being arranged on the vertical axis with APs having frequent roam events between them as being close to each other on the vertical axis, and APs having few or no roam events between them as distant from each other;

wherein the arranging of the APs (16) includes:

arranging the APs on the vertical axis with APs by evaluating a linear ordering problem (LOP) for a weighted undirected graph $G(V, E, W)$ where V is a set of nodes representing the set of APs of the wireless electronic data communication network, E is a set of undirected edges where $e_{ij} \in E$ is an edge connecting node $v_i \in V$ and $v_j \in V$, and W is a function that assigns edge weights to the edges of the set E wherein the edge weights have nonnegative values and the edge weight $w_{ij} \in W$ for the edge $e_{ij} \in E$ has a value corresponding to a handover frequency between the pair of APs represented by nodes $v_i, v_j \in V$ in historical roaming data for the wireless electronic data communication network.

* * * * *